United States Patent [19]

Dunski et al.

[11] Patent Number: 5,041,617

[45] Date of Patent: Aug. 20, 1991

[54] DITHIODIALKANOIC ACID ESTERS AND POLYMERS STABILIZED THEREWITH

[75] Inventors: Neil Dunski; Ali A. Bazzi, both of Creve Coeur; Henry J. Buehler, St. Louis, all of Mo.

[73] Assignee: Mallinckrodt Specialty Chemicals Company, St. Louis, Mo.

[21] Appl. No.: 158,000

[22] Filed: Feb. 19, 1988

Related U.S. Application Data

[63] Continuation of Ser. No. 798,251, Nov. 14, 1985, abandoned.

[51] Int. Cl.$^5$ .............................. C07C 321/00
[52] U.S. Cl. .................................. 560/147; 524/289
[58] Field of Search ..................... 560/147; 524/289

[56] References Cited

U.S. PATENT DOCUMENTS

| | | | |
|---|---|---|---|
| 2,623,066 | 12/1952 | Murphy et al. | 560/17 X |
| 3,398,116 | 8/1968 | Giolito | 560/154 X |
| 3,441,575 | 4/1969 | Dexter et al. | 560/4 X |
| 3,494,947 | 2/1970 | Schutze et al. | 560/154 |
| 4,108,830 | 8/1978 | Kline | 524/289 X |
| 4,123,436 | 10/1978 | Holub et al. | 524/289 |
| 4,132,702 | 1/1979 | Schmidt et al. | 524/84 |

OTHER PUBLICATIONS

Scott G., Atmospheric Oxidation and Antioxidants, Elsevier Publ. Co., Amsterdam, 1965, pp. 188–198.
Sawatari et al., Chem. Abst., vol. 82, No. 10, Abstract No. 59000w, 1975.
Neuriter et al., I and EC Product Research and Development, vol. 1, p. 236, 1962.

Primary Examiner—Jose G. Dees

[57] ABSTRACT

Multifunctional dithiodialkanoic acid esters useful in the stabilization of organic materials normally susceptible to oxidative degradation are prepared by contacting a selected dithiodialkanoic acid chloride with a selected 4-(3-hydroxypropyl)(mono- or di-alkyl) phenol under ester-forming reaction conditions. In a preferred embodiment, the ester is bis-3-(3',5'-di-t-butyl-4'-hydroxyphenyl)propyl dithiodipropionate.

1 Claim, No Drawings

DITHIODIALKANOIC ACID ESTERS AND POLYMERS STABILIZED THEREWITH

This is a continuation of application Ser. No. 798,251, filed Nov. 14, 1985 abandoned.

This invention relates to multifunctional dithiodialkanoic acid esters useful in the stabilization of organic materials normally susceptible to oxidative degradation, a process for preparing the esters and organic material stabilized with the esters.

Numerous compounds, including various sterically hindered phenol derivatives, have been proposed for stabilizing organic materials, such as organic polymers, against oxidative and thermal degradation.

Dexter et al, U.S. Pat. No. 3,441,575, discloses esters of di(lower)alkylhydroxyphenyl alkanoic acid formed with alcohols containing a divalent sulfur atom, a divalent oxygen atom or the divalent group —N(A)— wherein A is alkyl or alkanoyl as allegedly useful in the stabilization of organic material normally subject to oxidative deterioration. Polyolefins such as polyethylene, polypropylene, polybutylene, polyisoprene and copolymers thereof are included among materials which according to the patent are stabilized with such esters. One such ester is thio-bis-[ethylene3-(3,5-di-t-butyl-4-hydroxyphenyl)propionate], which is disclosed in Example 9 thereof. The latter compound, also known as thiodiethylene bis(3-(3',5'-di-t-butyl-4'-4-hydroxyphenyl)propionate, is a monosulfide represented by Formula I below:

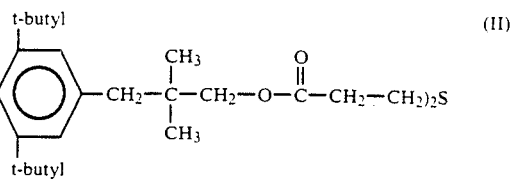

Schmidt et al., U.S. Pat. No. 4,132,702, discloses phenol esters allegedly useful for stabilizing organic material against thermo-oxidative degradation. The esters may be represented by the formula

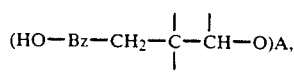

wherein Bz is a benzene ring having alkyl or aralkyl groups substituted in both positions ortho to the -OH group and substituted or unsubstituted positions meta to the -OH group; the carbon atoms indicated by the open bonds are bonded to hydrogen atoms or specified hydrocarbon or oxyhydrocarbon groups, provided that at least one such carbon atom is bonded through an indicated open bond thereof to such a group containing at least one carbon atom. The A moiety is a group derived from an organic or inorganic oxy-acid $A\text{-}(OH)_p$. One such ester disclosed therein is bis[3-(3',5'-di-t-butyl-4'-hydroxyphenyl)-2,-2-dimethylpropyl]thiodipropionate, which is the monosulfide represented by Formula II below:

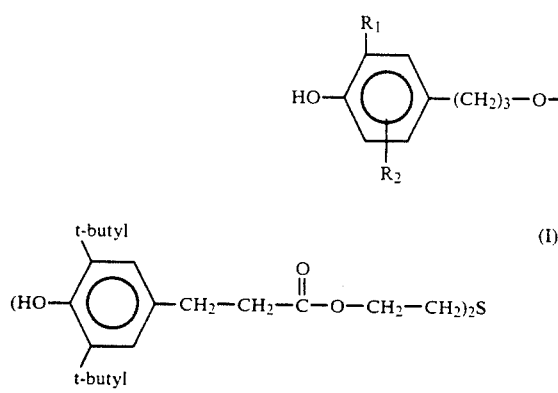

However, heretofore known compounds, such as the monosulfide compounds set forth above, have not been entirely satisfactory for stabilizing organic materials, such as polyolefins, (e.g., polyethylene and polypropylene) against oxidative and thermal degradation. Accordingly, there is a substantial need in the art for new compounds having improved capability of stabilizing organic materials such as polyethylene and polypropylene against such degradation.

It has now been found that the hereinafter described disulfides, which are hindered phenylhydroxyalkyl esters of dithiodialkanoic acids, have such improved stabilizing capabilities. Such acids are hereinafter sometimes referred to as DTDA acids.

DESCRIPTION OF THE INVENTION

Generally stated, the present invention provides disulfide compounds which may be represented by Formula III below:

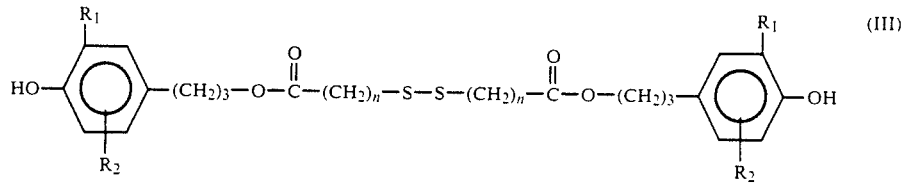

wherein n is an integer from 1 to about 10; $R_1$ is an alkyl group containing from one to 8 carbon atoms or a cycloalkyl group containing from 5 to 12 carbon atoms. $R_2$ is hydrogen, an alkyl group containing from one to 8 carbon atoms or a cycloalkyl group containing from 5 to 12 carbon atoms.

In another aspect, generally stated, the present invention provides a method for making the compounds of Formula III above, which comprises contacting a selected m,m'-di-thiodialkanoic acid chloride, where m is a number equal to the number of carbon atoms in each alkanoyl moiety of the acid chloride, with a selected 4-(3-hydroxypropyl)-(mono- or di-alkyl) phenol under ester-forming reaction conditions.

In still another aspect of this invention, there are provided organic compositions of matter stabilized against thermal-oxidative degradation, which comprise an organic material and a stabilizing amount of the compound of Formula III.

DETAILED DESCRIPTION OF THE INVENTION AND OF THE MANNER AND PROCESS OF MAKING AND USING IT

In the compounds of Formula III above where $R_2$ is other than hydrogen, in general each $R_2$ substituent is preferably located ortho to the hydroxyl group on its respective benzene ring, but may be in the meta position.

Suitable alkyl groups from which $R_1$ and $R_2$ may be selected include methyl, ethyl, propyl, isopropyl, butyl, amyl, hexyl, octyl, and the like. Included also are tertiary alkyl groups, such as t-butyl, t-amyl, t-octyl, and the like. Suitable cycloalkyl groups from which $R_1$ and $R_2$ may be selected include cyclopentyl, cyclohexyl, cyclooctyl, cyclododecyl, and the like. Preferably, $R_1$ and $R_2$ are t-butyl groups, with both $R_2$ groups located in their ortho positions. The number of $CH_2$ groups in the compounds is preferably such that, in Formula III above, n is from 2 to about 4 and most preferably is 2.

The DTDA acid ester compounds of this invention include, for example:

(a) bis-3-(3', 5'-di-t-butyl-4'-hydroxyphenyl)propyl dithiodiacetate;

(b) bis-3-(3',5'-di-t-butyl-4'-hydroxyphenyl)propyl dithiodipropionate;

(c) bis-3-(3',5'-di-t-butyl-4'-hydroxyphenyl)propyl dithiodibutyrate;

(d) bis-3-(3',5'-di-t-butyl-4'-hydroxyphenyl)propyl dithiodivalerate;

(e) bis-3-(3',5'-dimethyl-4'-hydroxyphenyl)propyl dithiodicaproate;

(f) bis-3-(3',5'-dicyclohexyl-4'-hydroxyphenyl)propyl dithiodipropionate;

(g) bis-3-(3',5'-di-t-amyl-4'-hydroxyphenyl)propyl dithiodipropionate; and (h) (3'-t-butyl-5'-methyl-4'-hydroxyphenyl)propyl, (3'',5''-di-t-butyl-4'-hydroxyphenyl)propyl dithiopropionate.

Preferred compounds of this invention are compounds (a), (b), (c) and (d) above. Compound (b) above is most preferred and may be represented by Formula IV below:

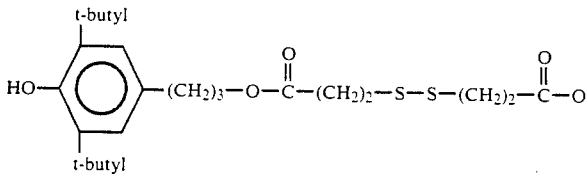 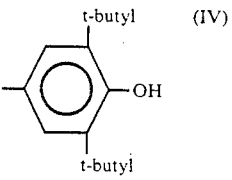 (IV)

The reaction is carried out in a solution containing the reactants and at least a solubilizing amount of a solvent for at least one, and preferably both, of the reactants. Suitable solvents include, for example, toluene, triethylamines, acetone, pyridine, dimethylformamide, water, methylethylketone, methylisobutylketone, dioxane, and the like.

Approximately stoichiometric amounts of the reactants, that is a molar ratio of about 2 moles of the 4-(3-hydroxypropyl)-(mono-or dialkyl)phenol per one mole of the dithiodiacid chloride, may be employed. The molar ratio is preferably at least 2:1 and, more preferably, is more than 2:1, e.g., up to about 2.4:1.

The reaction may be carried out at any suitable temperature, e.g., about 20°–25° C., and any suitable pressure, e.g., 760 mm Hg, for any suitable period, e.g., from about 0.5 to about 20 hours or more. Although the time required for completion of the reaction is dependent upon the particular reactants, solvent, temperature, and pressure employed, the reaction will, in general, be substantially complete within about 1 to about 10 hours.

Advantageously, the reaction is carried out with stirring and under an inert gaseous blanket, i.e., at least substantially inert to the reactants, solvent and products employed. Nitrogen is the preferred inert gaseous blanket.

Hydrogen chloride is liberated in the course of the reaction, and an alkaline material is used to neutralize the hydrogen chloride. Suitable alkaline materials which may be used to neutralize the hydrogen chloride include, for example, sodium or potassium hydroxide, sodium or potassium acetate, sodium or potassium carbonate, sodium or potassium bicarbonate, tertiary amines such as pyridine and triethylamine, and the like. Preferably, the alkaline material is triethylamine.

The order of addition of the reactants is not critical.

Dithiodialkanoic acid chlorides which can be used include, for example, acid chlorides of dithiodiacetic acid, dithiodipropionic acid, dithiodibutyric acid and the like. The dithio acid chlorides may be derived from their corresponding dithio acids (which are commercially available) by reaction thereof with a chlorinating agent, e.g. thionyl chloride.

The dithiodialkanoic acids may be prepared by well known procedures, for example, substantially in accordance with the procedures disclosed in Murphy et al., U.S. Pat. No. 2,623,066. These acids or their anhydrides may be used in lieu of the dithiodialkanoic acid chlorides in preparing the compounds of this invention. The dithio acids can be represented by Formula V below:

$$HOOC-(CH_2)_n-S-S-(CH_2)_n-COOH \qquad (V)$$

where n is as defined above.

The starting 4-(3-hydroxypropyl)-(mono- or dialkyl)phenols used in the present invention are well known compounds which can be prepared from phenol or simpler suitably substituted phenols by well known procedures.

The compounds of the present invention are useful as stabilizers of organic materials normally subject to oxidative deterioration. Such organic materials include, for example: synthetic organic polymeric substances such as vinyl resins formed from the polymerization of vinyl halides or from the copolymerization of vinyl halides with unsaturated polymerizable compounds, e.g., vinyl esters, alpha, beta-unsaturated aldehydes and unsaturated hydrocarbons such as butadienes and styrene; poly-alpha- olefins such as polyethylene (e.g., linear low density polyethylene), polypropylene, polybutylene (e.g., polybutene-1), polyisoprene, and the like, including copolymers of poly-alpha-olefins, polyurethanes, polyamides such as polyhexamethylene adipamide and polycaprolactam; polyesters such as polymethylene terephthalates; polycarbonates, polyacetals; polystyrene; polyethyleneoxide; and copolymers such as those of high impact polystyrene containing copolymers of butadiene and styrene and those formed by the copolymerization of acrylonitrile, butadiene and/or styrene. Other materials which can be stabilized by the active compounds of the present invention include lubrication oil of the aliphatic ester type, i.e., di(2-ethylhexyl)-azelate, pentaerythritol tetracaproate, and the like; animal and vegetable derived oils, e.g., linseed oil, fat, tallow, lard, peanut oil, cod liver oil, castor oil, palm oil, corn oil, cotton-seed oil, and the like; hydrocarbon materials such as gasoline, mineral oil, fuel oil, drying oil, cutting fluids, waxes, resins and the like, fatty acids, soaps and the like.

The compounds of this invention (represented by Formula III above) may be employed in any stabilizing amount as stabilizers for organic materials normally susceptible to oxidative degradation. Such amount may be for example, from about 0.005% to about 10% by weight of the stabilized composition. For polyolefins, e.g., linear low density polyethylene, polypropylene and poly(butene-1), such amount is preferably from about 0.05% to about 5% and more preferably from about 0.1% to about 1%.

The compounds of this invention may be used alone or in combination with other stabilizers or additive materials, such as dilauryl-beta-thiodipropionate and distearyl-beta-thiodipropionate.

Other antioxidants, antiozonants, thermal stabilizers, ultraviolet light absorbers, coloring materials, dyes, pigments, metal chelating agents, etc. may also be used in the compositions of the invention.

Phosphite esters may also be used in stabilized compositions containing the novel antioxidant compounds of the present invention. Such phosphite esters include dialkyl phosphites (for example, distearyl phosphite, dilauryl phosphite, and the like e.g., trialkyl phosphites (for example, trilauryl phosphite, tris(ethylhexyl) phosphite, and the like); and tris(alkaryl) phosphites (for example tris(nonylphenyl)phosphites, and the like).

The compounds of this invention are especially useful for stabilizing polymeric materials such as polyolefins and the like, e.g., polyethylene (especially linear low density polyethylene, i.e., LLDPE), polypropylene, poly(butene-1), and the like.

Stabilized compositions of matter of this invention may be prepared by incorporating the compounds into the organic material to be stabilized using well known methods for incorporating stabilizers into such material. For example, in general, the stabilizer may simply be physically admixed with the organic material.

It is well known that upon processing polyethylenes at elevated temperature, cross-linking takes place. This results in an apparent increase in molecular weight and hence lower melt index values. More importantly, it also results in a change in molecular weight distribution by increasing, due to cross-linking, the high molecular weight tail. In many applications, it is desired that polyethylene not cross-link while being processed. Accordingly, a feature of a good stabilizer is that the melt index does not appreciably decrease when working a polyethylene as in extrusion operations.

In contrast to polyethylenes, polypropylene typically undergoes chain scission during processing thereof at elevated temperatures, i.e. a reduction in apparent molecular weight. This is reflected typically in melt flow rate values which increase as the molecular weight decreases.

Practice of the present invention is illustrated by the following non-limiting examples. All parts, percents and other amounts given throughout this disclosure, including the examples which follow, are by weight unless otherwise indicated.

EXAMPLE 1

Bis-3-(3',5'-di-t-butyl-4-hydroxyphenyl)propyl dithiodipropionate

To 24 g (0.114 mole) of 3,3'-dithiodipropionic acid was added 72 g (0.56 mole) thionyl chloride and the resulting mixture was heated with stirring for 2 hours at 75° C., at the end of which time the excess thionyl chloride was stripped off. The residue was then dissolved in 200 ml of toluene and the resulting solution was slowly added with stirring to a solution of 60 g (0.228 mole) of 4-(3-hydroxypropyl)-2,6-di-tert-butylphenol and 18 g (0.228 mole) of pyridine in 500 ml of toluene. The resulting reaction was mildly exothermic. After the addition was complete, the resulting mixture was stirred for 2 hours. The pyridine HCl salts were removed by filtration and the clear filtrate washed several times with water. The washed solution was dried over anhydrous $MgSO_4$. Filtration and removal of the solvent yielded an oil which was rinsed with hot hexane and cooled to afford the above compound in 92% yield as a white solid melting at 65° C. The structure of this new compound was confirmed by IR, $^1H$ and $^{13}C$ NMR spectroscopic analyses and is represented by Formula IV above.

EXAMPLE 2

Linear Low Density Polyethylene

In this Example, the composition of Example 1 (hereinafter Compound I) was tested for capability of stabilizing linear low density polyethylene (LLDPE, Union Carbide Corporation) against oxidative and thermal degradation. For comparative purposes, a test sample of the LLDPE to which no compound was added was also tested. In addition, also for comparative purposes, the above Dexter et al. monosulfide of Formula I (hereinafter referred to as compound II) and the above Schmidt et al. monosulfide of Formula II (hereinafter referred to as compound III) were also tested. 0.7 g of each of the compounds (compound I. compound II and compound III) was blended with a separate sample (700 g) of linear low density polyethylene, LLDPE, (melt index 1.0) devoid of any added antioxidant. Each of the resulting blends as well as the LLDPE without any antioxidant added was extruded twice at 160° C. in a ¾" Brabender extruder. The extruder speed was set at 50 rpm. Each extruded rod was pelletized prior to reextrusion. Following the two compounding passes at 160° C. each sample was extruded 5 times at 260° C. and 50 rpm, with each extruded rod being water quenched and pelletized prior to reextrusion. The melt index was then determined according to ASTM D1238 condition E (190° C., 2160 g) on each of the pelletized samples following the first, third and fifth extrusion at 260° C. Samples from the second extrusion at 160° C. were compression molded at 170° C. and 10 tons pressure into plaques of 25 mils thickness.

Twelve chips, each about 1 inch in diameter, were cut from each plaque and placed in a 150° C. air circulating oven. Time to degradation was determined for these chips. As is well known to those skilled in the art, the "time to degradation" in such oven aging test is the time at which substantially the entire sample becomes discolored and brittle.

The following results were obtained:

| Anti-oxidant | Melt Index, g/10 min. ASTM D1238 Condition E | | | Hours To Degradation at 150° C. |
| --- | --- | --- | --- | --- |
| | 1st Extrusion at 260° C. | 3rd Extrusion at 260° C. | 5th Extrusion at 260° C. | |
| None | 0.61 | 0.38 | 0.29 | 24 |
| Compound I | 0.90 | 0.86 | 0.80 | 512 |
| Compound II | 0.89 | 0.78 | 0.63 | 240 |
| Compound III | 0.85 | 0.84 | 0.75 | 504 |

The results show better retention of melt index during processing as well as better long term oven stability for Compound I (a compound of this invention), compared to comparative compounds II and III.

EXAMPLE 3

Polypropylene

In this Example, the test set forth in Example 2 was repeated except that the polypropylene was substituted for the polyethylene.

0.7 g of each of compound I, compound II and compound III, and 0.7 g calcium stearate, were blended with 700 g Profax 6501 polypropylene. In a similar manner to that described in Example 2 for LLDPE, these blends were extruded twice at 160° C. and four times at 260° C. Samples from the second 160° C. extrusion were compression molded at 170° C. into plaques of 25 mils thickness. Strips were cut out of the plaques and placed in a 150° C. air circulating oven to determine time to degradation. Melt flow rate was determined for samples from each of the 260° C. extrusions according to ASTM D1238 condition L (230° C., 2160 g).

The results obtained were as follows:

| Anti-oxidant | Melt Flow Rate, g/10 min ASTM D1238 Condition L | | | | Hours to Degradation at 150° C. |
| --- | --- | --- | --- | --- | --- |
| | 1st Extrusion at 260° C. | 2nd Extrusion at 260° C. | 3rd Extrusion at 260° C. | 4th Extrusion at 260° C. | |
| None | 10.2 | 15.7 | 23.7 | — | 48 |
| Cpd.I | 2.4 | 3.7 | 5.6 | 7.2 | 600 |
| Cpd.II | 2.6 | 3.8 | 6.0 | 8.9 | 432 |
| Cpd.III | 2.7 | 3.8 | 6.2 | 9.0 | 528 |

BEST MODE CONTEMPLATED

The best mode contemplated for carrying out this invention has been set forth in the above description, for example, by way of setting forth preferred materials and operating conditions, including but not limited to preferred ranges and values of amounts and other non-obvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. The compound bis-3-(3',5'-di-tert-butyl-4'-hydroxyphenyl)propyl dithiodipropionate.

* * * * *